United States Patent [19]

Siwek

[11] Patent Number: 4,615,339
[45] Date of Patent: Oct. 7, 1986

[54] PEDIATRIC ARM RESTRAINING DEVICE

[76] Inventor: Melinda L. Siwek, 11857 Averill Ct., Riverside, Calif. 92503

[21] Appl. No.: 624,133

[22] Filed: Jun. 25, 1984

[51] Int. Cl.$^4$ .............................................. A61F 13/00
[52] U.S. Cl. .................................. 128/133; 128/87 R
[58] Field of Search ............... 128/133, 165, DIG. 15, 128/87 R, 134; 2/252, 255

[56] References Cited

U.S. PATENT DOCUMENTS

| | | | |
|---|---|---|---|
| 2,279,296 | 4/1942 | Bresnick et al. | 128/133 |
| 2,468,580 | 2/1949 | Weis et al. | 2/255 |
| 3,462,764 | 8/1969 | Caster | 2/252 |
| 3,533,407 | 10/1970 | Smith | 128/165 |
| 4,206,512 | 6/1980 | Osborne | 128/134 |
| 4,379,463 | 4/1983 | Meier et al. | 128/DIG. 15 |
| 4,470,410 | 9/1984 | Elliott | 128/133 |
| 4,481,942 | 11/1984 | Duncan | 128/133 |
| 4,489,718 | 12/1984 | Martin | 128/88 |

Primary Examiner—Robert P. Swiatek
Assistant Examiner—David L. Tarnoff
Attorney, Agent, or Firm—Harvey S. Hertz

[57] ABSTRACT

A device formed as a sleeve from a flat fabric rectangle with engaging VELCRO attachment strips along opposite edges and sides of the rectangle. The VELCRO strips are overlapping to provide circumferential adjustment to the arm upon application and quick detachment. The sleeve may be formed over either arm in a length overlapping the elbow and extending from the wrist to nearly the shoulder of the wearer. A thumb hole and integral longitudinal pockets are provided, the pockets for receiving stiffening strips as needed. A tie-down ring is also provided for external restraint.

4 Claims, 4 Drawing Figures

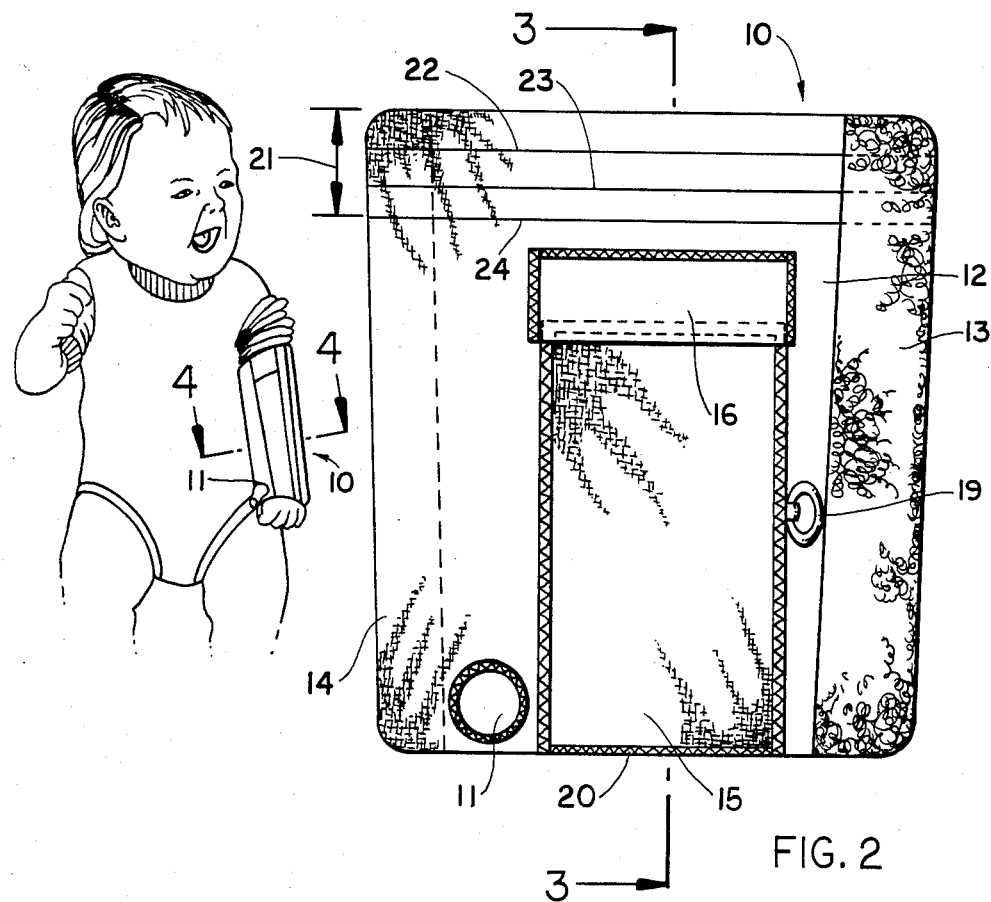
FIG. 1
FIG. 2
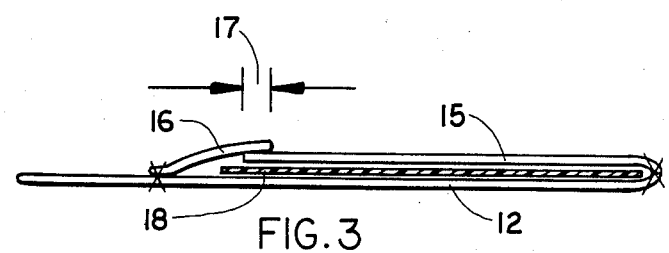
FIG. 3
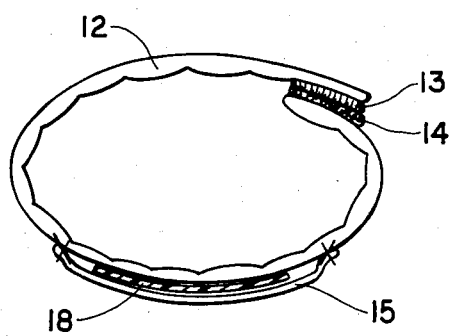
FIG. 4

PEDIATRIC ARM RESTRAINING DEVICE

BACKGROUND OF THE INVENTION

The invention relates to arm restraints, particularly for pediatric use. Various medical and habit problems indicate the use of such a restraining device, and various solutions are extant in the prior art. Surgery on the face or mouth for the correction of malformations or accident damage, or the treatment of burns or other medical conditions for a child require measures preventing hand contact. A very young child cannot be expected to understand the need to refrain from interference with affected upper body areas, hence the need for a mechanical restraint. Moreover, mechanical restraints are useful in breaking a thumb sucking habit or preventing interference with intubation.

In the prior art, the general class of devices including splints, surgical binders and arm and waist supports are suggestive of approaches to the pediatric arm restraint problem. However, prior art apparatus generally fails to provide quick application with circumferential tolerance to accommodate variations in arm size and quick removal, or symmetry such that a single design fits either arm. The prior art is also deficient in respect to combinations including provision for optional longitudinal stiffening, external tie-down provisions and other features of particular applicability for pediatric uses.

The prior art know to the applicant consists of U.S. Pat. Nos. 4,309,991; 4,047,250; 3,533,407; 3,279,459; 2,943,859 2,206,404; 3,902,503; and 3,238,939.

The devices of U.S. Pat. Nos. 3,279,459 and 2,943,859 are typical of the inflatable "cuff," the former relating to the well-known blood pressure cuff and the latter applying as an arm stiffener for a golfer. Inflatable devices generally are not advantageous for application for arm restraint applied to a small child or infant because of the possibility of long-term leakage deflation (over night, for example). Moreover, the small child may not be able to cooperate with the practitioner to achieve the optimum degree of inflation. Obviously, excessive inflation can restrict blood circulation in an arm.

Arm or wrist braces or splints shown in U.S. Pat. Nos. 2,206,404 and 4,047,250 show thumb holes or spaces, the former showing a laced sleeve and the latter showing a typical VELCRO attachment. The VELCRO attachment is much to be preferred over the laced sleeve because of the quick application and detachment it provides. VELCRO attachment is also used in the combination of the invention.

The typical prior art combinations which may be regarded as generally adapted for modification in dimensional aspects to serve as small child arm restraints are not flexible in design so that a single design fits either the left or right arm or provides the highly desirable quick application and removal feature and longitudinal accommodation.

The manner in which the invention overcomes the disadvantage of the prior art to produce a novel device which is both effective and inexpensive will be understood as this description proceeds.

SUMMARY OF THE INVENTION

In accordance with the foregoing, it may be said to have been the general object of the invention to provide a pediatric arm restraining device which is simple in design, able to be used on either arm, able to accommodate arm size variations, safe in the event of falling by a child wearing the device, and, finally, is low in cost.

The device of the invention is formed in a flat, generally rectangular shape of padded or quilted fabric and is rolled about an arm to form a sleeve. VELCRO strips along opposite edges (and opposite flat faces) of the rectangular shape are relatively wide to allow attachment with a degree of variation in circumference of the sleeve. Thus only a single thumb hole location, a given flat surface of the rectangle being rolled internally or externally in the sleeve shape, depending upon which arm is to be fitted with the restraining device.

A stiffener pocket with overlapping flap provides for the insertion of one or more elongated strip-like stiffeners, preferably of a resilient material (plastic for example), which would not resist bending from the force of a fall, but would stiffen the sleeve against elbow and wrist flexing as a voluntary arm movement.

The term VELCRO used herein is a trademark widely associated with "hook-and-pile" fibrous fastener elements. One of the attaching strips described contains the "pile" in relatively stiff fibers resembling a carpet. The other strip includes the "hook" elements comprising a large plurality of hook-shaped fibers. These strips mate together firmly, but not inseparably upon being pressed together. Disengagement is effected by a hand "peeling" force. U.S. Pat. No. 4,047,250 is a specific reference identifying and defining VELCRO.

Other features and advantages of the novel combination will be realized as this description proceeds.

BRIEF DESCRIPTION OF THE DRAWINGS

FIG. 1 is a pictorial view showing the restraining device of the invention worn on one arm of a small child.

FIG. 2 is a flat rectangular layout of the sleeve ready to be rolled and attached to an arm.

FIG. 3 is a sectional view taken as indicated on FIG. 2.

FIG. 4 is a sectional view of the device rolled and attached, taken as indicated on FIG. 1.

DETAILED DESCRIPTION

Referring now to FIG. 1, the device according to the invention is shown generally at 10. Although only one arm is shown wearing the device, it will be understood that either or both arms could be so fitted, as required. The thumb hole 11 receives the child's thumb, the hole being edge bound with soft yarn or the like to provide a comfortable non-abraiding fit. The other end of the device 10 extends to near the wearer's shoulder.

In FIG. 2, the flat generally rectangular form of the device as manufactured is shown. The body of the rectangle is of quilted or padded material with special attention to comfort in contact with the arm. VELCRO strip 13 is shown sewn or otherwise attached to the face of the rectangular body 12, whereas VELCRO strip 13 is similarly attached to the opposite face of 12. In accordance with that arrangement, the sleeve can be rolled with either body face 12 outward and the VELCRO attachment secured as shown in FIG. 4.

Of course, it makes no difference whether strip 13 is the "pile" element and strip 14 the "hook" element or vice verse.

A sewn on (or otherwise attached) piece 15 forms a pocket between itself and body 12, the open end thereof being covered by an overlapping flap 16. The section shown in FIG. 3 clarifies this structure, the amount of overlap being represented at 17. This flap overlap serves to keep the stiffener element 18 confined within the pocket. The flap, being of a textile material similar to piece 15, is easily deformed to facilitate installation and removal of stiffener 18.

It is, of course, true that the pocket between 12 and 15 could be divided (by stitching or otherwise) so as to form plural parallel longitudinally extending pockets each receiving a narrower elongated stiffening member.

In FIG. 4, stiffening member 18 is represented as one piece.

A ring 19 of metal, plastic, or fabric is conventionally attached to the edge of piece 15 as shown. This ring is used to tie the restrainer to a bed rail or the like, if necessary This ring could be located along the edge 20 in which case it would be available irrespective of which way the flat body is rolled to form sleeve 10.

A margin of additional body material 21 may be provided to allow for tailored longitudinal length of sleeve 10. The sewn lines 22,23, and 24 are each preferably double lines for stitching, so that trimming between these lines for length selection will not leave an unbound edge.

Variations and modifications are obviously possible and it is not intended that the scope of the invention be regarded as limited by the drawing or this description, these being intended to be typical and illustrative only. In using the terms rectangular or generally rectangular, it is to be understood that the flat fabric body 12 may be slightly trapezoidal (i.e., its opposite sides may not be precisely parallel), and it may have rounded corners as illustrated in FIG. 2. Padded material as referred to in the claims includes the quilted form.

I claim:

1. A pediatric arm restraining device comprising:
    a generally flat, generally rectangular body of padded fabric material having a longitudinal dimension corresponding to the length dimension of the portion of an arm overlapping the elbow onto which it is to be fitted, said rectangular body having a width dimension allowing a predetermined amount of overlap when said flat body is rolled over said arm forming a sleeve having an elongated dimension corresponding to the length dimension of said arm and overlapping the elbow;
    an elongated hook fastener strip affixed along a first edge of a first surface of said rectangular body, said fastener strip having a first predetermined width within said body width dimension overlap;
    an elongated pile fastener strip affixed along a second edge of said surface of said rectangular body opposite said first edge, said pile fastener strip extending generally parallel to said hook fastener strip and having a second predetermined width within said body width dimension overlap such that said hook and pile fastener strips are in position to be mated as said sleeve is formed, said sleeve having an elongated dimension corresponding to said arm lenght dimension;
    a pocket formed along one of said first and second surfaces of said rectangular body, said pocket being elongated in a dimension corresponding to said sleeve elongated dimension, said pocket is formed by an additional fabric piece affixed to one of said body surfaces along the two elongated edges of said piece and one of the other edges thereof;
    at least one elongated stiffener element inserted within said pocket enhanced rigidity of said sleeve against elbow bending, said pocket has an open end in the direction of said sleeve elongated dimension and a flap is affixed with predetermined overlap at said pocket open end, said flap and said pocket open end being deformable to emplace and remove said stiffener element;
    a portion of said rectangular body extends in said longitudinal at the end of said body corresponding to the upper arm end of said sleeve in order to provide a trimmable portion, said trimmable portion having at a least one pair of sewn lines for cutting between said lines for adapting said device for a shorter arm length, and thereby leaving said end of said body with a sewn edge;
    and a thumb hole through said rectangular body adjacent one of said fastener strips and closely adjacent the longitudinal end of said rectangular body, said thumb hole thereby accommodating the right or left thumb when said sleeve is emplaced with one of said first and second surfaces of said body outward, and thereby permitting protrusion of fingers from said sleeve.

2. The device defined in claim 1 in which said hook and pile fastener strips are VELCRO strips.

3. The device according to claim 1 in which at least one tie-down ring is attached to a portion of said rectangular body to facilitate external attachment to a bed rail or the like.

4. The device according to claim 1 in which said stiffener element is resilient and sufficiently flexible to permit bending of said sleeve in the event of falling of the wearer.

* * * * *